(12) United States Patent
Nygaard

(10) Patent No.: US 9,486,840 B2
(45) Date of Patent: Nov. 8, 2016

(54) HIGH-SPEED, TRIANGULATION-BASED, 3-D METHOD AND SYSTEM FOR INSPECTING MANUFACTURED PARTS AND SORTING THE INSPECTED PARTS

(71) Applicant: GII ACQUISITION, LLC, Davisburg, MI (US)

(72) Inventor: Michael G. Nygaard, Fenton, MI (US)

(73) Assignee: GII Acquisition, LLC, Davisburg, MI (US)

( * ) Notice: Subject to any disclaimer, the term of this patent is extended or adjusted under 35 U.S.C. 154(b) by 315 days.

(21) Appl. No.: 13/901,868

(22) Filed: May 24, 2013

(65) Prior Publication Data

US 2014/0346094 A1    Nov. 27, 2014

(51) Int. Cl.
| | | |
|---|---|---|
| *B07C 5/00* | (2006.01) |
| *B07C 5/342* | (2006.01) |
| *G01N 21/88* | (2006.01) |
| *G01N 21/952* | (2006.01) |
| *G01N 21/84* | (2006.01) |

(52) U.S. Cl.
CPC ......... *B07C 5/3422* (2013.01); *G01N 21/8806* (2013.01); *G01N 21/952* (2013.01); *B07C 2501/0009* (2013.01); *G01N 2021/845* (2013.01)

(58) Field of Classification Search
CPC ..... B07C 5/342; B07C 5/3425; B07C 5/366; B07C 5/3416; G01B 11/16; G01B 11/24; G01B 11/2518; G01B 11/026; G01S 17/48
USPC .................. 209/576, 577, 587–589; 356/602
See application file for complete search history.

(56) References Cited

U.S. PATENT DOCUMENTS

| | | |
|---|---|---|
| 2,645,343 A | 7/1953 | Nemir |
| 3,770,969 A | 11/1973 | Ansevin et al. |
| 3,924,953 A | 12/1975 | Allard |
| 4,239,969 A | 12/1980 | Haas et al. |
| 4,315,688 A | 2/1982 | Pryor |
| 4,547,674 A | 10/1985 | Pryor et al. |

(Continued)

FOREIGN PATENT DOCUMENTS

| | | |
|---|---|---|
| WO | 2005022076 A2 | 3/2005 |
| WO | 2009130062 A1 | 10/2009 |

OTHER PUBLICATIONS

International Search Report and Written Opinion; International application No. PCT/US2014/016663; date of mailing May 28, 2014.

(Continued)

*Primary Examiner* — Joseph C Rodriguez
*Assistant Examiner* — Kalyanavenkateshware Kumar
(74) *Attorney, Agent, or Firm* — Brooks Kushman P.C.

(57) ABSTRACT

High-speed, triangulation-based, 3-D method and system for inspecting manufactured parts and sorting the inspection parts are provided. A plurality of angularly-spaced, triangulation-based, sensor heads are located at an imaging station to simultaneously deliver focused lines of radiation onto a plurality of exterior side surfaces of the part during motion of the part relative to the focused lines to obtain corresponding arrays of reflected lines of radiation. The sensor heads simultaneously sense their corresponding arrays of reflected lines to obtain corresponding sets of 2-D profile signals. Each set of profile signals represent a 3-D view of one of the exterior side surfaces and the sets of 2-D profile signals represent a 360° panoramic composite 3-D view of the outer peripheral surface of the part.

20 Claims, 7 Drawing Sheets

(56) References Cited

U.S. PATENT DOCUMENTS

| | | | |
|---|---|---|---|
| 4,598,998 A | 7/1986 | Kamei et al. |
| 4,644,394 A | 2/1987 | Reeves |
| 4,721,388 A | 1/1988 | Takagi et al. |
| 4,831,251 A | 5/1989 | Hanna |
| 4,852,983 A | 8/1989 | Fein |
| 4,906,098 A | 3/1990 | Thomas et al. |
| 4,923,066 A | 5/1990 | Ophir et al. |
| 4,969,746 A | 11/1990 | McConnell et al. |
| 4,970,401 A | 11/1990 | Sadeh et al. |
| 4,983,043 A | 1/1991 | Harding |
| 5,012,117 A | 4/1991 | Karafa et al. |
| 5,024,529 A | 6/1991 | Svetkoff et al. |
| 5,098,031 A | 3/1992 | Hitomi |
| 5,164,995 A | 11/1992 | Brooks et al. |
| 5,168,458 A | 12/1992 | Gomes |
| 5,170,306 A | 12/1992 | Gomes |
| 5,291,272 A | 3/1994 | Demirsu |
| 5,383,021 A | 1/1995 | Hanna |
| 5,431,289 A | 7/1995 | Hoffman |
| 5,521,707 A | 5/1996 | Castore et al. |
| 5,531,316 A | 7/1996 | Savino |
| 5,546,189 A | 8/1996 | Svetkoff et al. |
| 5,568,263 A | 10/1996 | Hanna |
| 5,608,530 A | 3/1997 | Gates |
| 5,617,209 A | 4/1997 | Svetkoff et al. |
| 5,646,724 A | 7/1997 | Hershline |
| 5,815,275 A | 9/1998 | Svetkoff et al. |
| 5,847,382 A | 12/1998 | Koch et al. |
| 6,046,462 A | 4/2000 | Yokajty et al. |
| 6,055,329 A | 4/2000 | Mufti |
| 6,098,031 A * | 8/2000 | Svetkoff et al. ............ 702/159 |
| 6,252,661 B1 | 6/2001 | Hanna |
| 6,285,034 B1 | 9/2001 | Hanna et al. |
| 6,289,600 B1 | 9/2001 | Watts |
| 6,313,948 B1 | 11/2001 | Hanna |
| 6,959,108 B1 | 10/2005 | Bartelt et al. |
| 7,123,765 B2 | 10/2006 | Carbone, II et al. |
| 7,134,544 B1 | 11/2006 | Kilper et al. |
| 7,312,607 B2 | 12/2007 | Nygaard |
| 7,363,817 B2 | 4/2008 | Bond et al. |
| 7,403,872 B1 | 7/2008 | St. Onge et al. |
| 7,633,046 B2 | 12/2009 | Spalding |
| 7,633,634 B2 | 12/2009 | Spalding et al. |
| 7,633,635 B2 | 12/2009 | Nygaard et al. |
| 7,684,054 B2 | 3/2010 | Crowther |
| 7,738,088 B2 | 6/2010 | Spalding |
| 7,738,121 B2 | 6/2010 | Spalding |
| 7,755,754 B2 | 7/2010 | Spalding |
| 7,777,900 B2 | 8/2010 | Nygaard et al. |
| 7,796,278 B2 | 9/2010 | Spalding et al. |
| 8,054,460 B2 | 11/2011 | Agapiou et al. |
| 8,179,434 B2 | 5/2012 | Koval et al. |
| 8,228,493 B2 | 7/2012 | Yagyu et al. |
| 8,390,826 B2 | 3/2013 | Walstra |
| 8,570,504 B2 | 10/2013 | Nygaard |
| 8,615,123 B2 | 12/2013 | Dabic |
| 2001/0021026 A1 | 9/2001 | Liu |
| 2005/0174567 A1 | 8/2005 | Hanna |
| 2006/0236792 A1 | 10/2006 | Hanna |
| 2007/0223009 A1 | 9/2007 | Erfling et al. |
| 2009/0103107 A1 | 4/2009 | Nygaard |
| 2009/0103112 A1 | 4/2009 | Nygaard |
| 2009/0107896 A1 | 4/2009 | Gochar, Jr. |
| 2010/0084245 A1 | 4/2010 | Gonzalez Alemany et al. |
| 2010/0201806 A1 | 8/2010 | Nygaard et al. |
| 2010/0245850 A1 | 9/2010 | Lee et al. |
| 2011/0005899 A1 | 1/2011 | Grzelak |
| 2012/0105429 A1 | 5/2012 | Nygaard |
| 2012/0285751 A1 | 11/2012 | Turner |
| 2012/0293623 A1 | 11/2012 | Nygaard |
| 2012/0293789 A1 | 11/2012 | Nygaard |
| 2012/0303157 A1 | 11/2012 | Chung |
| 2013/0235371 A1 | 9/2013 | Nygaard et al. |
| 2014/0043610 A1 | 2/2014 | Engel et al. |
| 2014/0063509 A1 | 3/2014 | Nygaard et al. |
| 2014/0168661 A1 | 6/2014 | Nygaard et al. |

OTHER PUBLICATIONS

International Search Report and Written; International application No. PCT/US14/16662; date of mailing Dec. 8, 2014.

Notice of Allowance and Fee(s) Due; U.S. Appl. No. 14/221,410; date of mailing Dec. 5, 2014.

International Search Report and Written Opinion; International application No. PCT/US2015/016307; date of mailing Jun. 3, 2015.

Brosed, Francisco Javier, et al.; 3D Geometrical Inspection of Complex Geometry Parts Using a Novel Laser Triangulation Sensor and a Robot; Sensors 2011, 11, 9-110; doi:10.3390/s110100090; published Dec. 23, 2010.

Yogeswaran, Arjun; 3D Surface Analysis for the Automated Detection of Deformations on Automotive Panels; Ottawa-Carleton Institute for Electrical and Computer Engineering School for Information Technology and Engineering, University of Ottawa; Apr. 2011.

Notice of Allowance and Fee(s) Due; corresponding U.S. Appl. No. 14/449,361; date mailed Sep. 8, 2015.

Office Action; related U.S. Appl. No. 14/449,361; notification date May 15, 2015.

International Preliminary Report on Patentability; related PCT application serial No. PCT/US2014/016662; date of issuance of report Nov. 24, 2015.

International Preliminary Report on Patentability; related PCT application serial No. PCT/US2014/016663; date of issuance of report Nov. 24, 2015.

International Search Report and Written Opinion; International application No. PCT/US15/34349; date of mailing Sep. 15, 2015.

* cited by examiner

HIGH-SPEED, TRIANGULATION-BASED, 3-D METHOD AND SYSTEM FOR INSPECTING MANUFACTURED PARTS AND SORTING THE INSPECTED PARTS

CROSS-REFERENCE TO RELATED APPLICATIONS

This application is related to U.S. patent application entitled "High-Speed, Triangulation-Based, 3-D Method and System For Inspecting Manufactured Parts and Sorting the Inspected Parts" filed on the same day as this application and having U.S. Ser. No. 13/901,862.

TECHNICAL FIELD

This invention relates in general to the field of non-contact, optical inspection and sorting of parts and, more particularly, to triangulation-based, 3-D methods and systems for optically inspecting and sorting parts, such as ammunition cases and threaded fasteners.

OVERVIEW

Traditional manual, gauging devices and techniques have been replaced to some extent by automatic inspection methods and systems. However, such automatic inspection methods and systems still have a number of shortcomings associated with them.

Many parts, such as fasteners and ammunition cartridges and cases develop cracks, splits, or other outer surface defects during the manufacturing process. While parts can be rotated about their axes during the inspection process, this adds additional time to the process.

In optical metrology, inter-reflection (i.e., double bounce or secondary reflection) poses a challenge for surface measurement of shiny objects. Due to specular reflections that can occur among concave surfaces or combinations of surfaces positioned near right angles to each other, the true desired laser lines are often obscured by inter-reflection lines. Such obscuration makes it difficult to measure shiny surfaces of complex surface geometry.

Laser triangulation measuring equipment generally operate by projecting, with a laser beam having a wavelength centered at approximately 830 nm (infrared (IR) radiation), a light spot having a preset spot size onto the surface to be examined, e.g., from a laser projection "gun" that may be mounted normal to the surface being examined. A light detection unit including a lens and a light detecting element or "camera," such as a CCD or CMOS imaging chip or a position sensing device (PSD), e.g., of silicon, at an offset angle to the projection axis may observe the position of the laser spot in its field of view and output a signal describing the angle at which the spot appeared in the field of view. The range to the object can be computed from the angle information when the distance between the laser projection axis and the light detection unit is known. The offset angle between the laser beam and the line of sight of the light detection unit is often referred to as the "triangulation angle." Based on which part of the detector the light reflected from the imaged object impinges, the height or "z-component" of the object at the point at which the light spot impinges upon the object may be determined.

Inspection of defects on and in small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the U.S. Department of Defense, MIL-STD-636. For small arms ammunition calibers up to 0.50, this standard serves to evaluate and illustrate a practical majority of defects assembled as a result of extensive surveys covering all the small arms ammunition manufacturing facilities in the United States.

FIG. 1a is a side schematic view of a .50 caliber case. As explained in the above-noted military standard, a case is counted as a defective because of a split case if the cartridge case shows a definite separation of the metal entirely through the case wall. A case is classified as either a "major" or "critical" defect depending on the location of split. A split in the (I), (S) or (J) position is counted as a "major" defect when no loss of powder occurs; and as a "critical" defect when loss of powder occurs. A split in the (K), (L) or (M) position is counted as a "critical" defect.

FIG. 1b is a side schematic view of a .30 caliber case. As noted above, a case is counted as a defective because of a split case if the cartridge case shows a definite separation of the metal entirely through the case wall. A case is classified either as "major" or "critical" defective depending on location of split. A split in the (I) of (J) position is counted as a "major" defect when no loss of powder occurs; and as a "critical" defect when loss of powder occurs. A split in the (K), (L), or (M) position is counted as a "critical" defect.

FIG. 1c is a side schematic view of a .45 caliber case. Again, as noted above, a case is counted as defective because of a split case if the cartridge case shows a definite separation of the metal entirely through the case wall. A case is classified either as a "major" or "critical" defective depending on the location of the split. A split in the (I) or (J) position is counted as a "major" defect when no loss of powder occurs; and as a "critical" defect when loss of powder occurs. A split in the (K), (L), or (M) position is counted as a "critical" defect.

U.S. Pat. No. 4,923,066 discloses an automatic visual inspection system for small arms ammunition which sorts visual surface flaws at high speed according to established standards which can be tailored to fit specific needs.

U.S. Pat. No. 7,403,872 discloses a method and system for inspecting manufactured parts such as cartridges and cartridge cases and sorting the inspected parts.

WO 2005/022076 discloses a plurality of light line generators which generate associated beams of light that intersect a part to be inspected.

U.S. Pat. No. 6,313,948 discloses an optical beam shaper for production of a uniform sheet of light for use in a parts inspection system having a light source including a coherent light generator, a diffractive beam shaper, and lens elements.

U.S. Pat. No. 6,285,034 discloses an inspection system for evaluating rotationally asymmetric workpieces for conformance to configuration criteria.

U.S. Pat. No. 6,252,661 discloses an inspection system for evaluating workpieces for conformance to configuration criteria.

U.S. Pat. No. 6,959,108 discloses an inspection system wherein workpieces to be inspected are consecutively and automatically launched to pass unsupported through the field of view of a plurality of cameras.

U.S. Pat. No. 4,831,251 discloses an optical device for discriminating threaded workpiece by the handedness by their screw thread profiles.

U.S. Pat. No. 5,383,021 discloses a non-contact inspection system capable of evaluating spatial form parameters of a workpiece to provide inspection of parts in production.

U.S. Pat. No. 5,568,263 also discloses a non-contact inspection system capable of evaluating spatial form parameters of a workpiece to provide inspection of parts in production.

U.S. Pat. No. 4,852,983 discloses an optical system which simulates the optical effect of traveling over a large distance on light traveling between reference surfaces.

U.S. Patent Application Publication No. 2005/0174567 discloses a system to determine the presence of cracks in parts.

U.S. Patent Application Publication No. 2006/0236792 discloses an inspection station for a workpiece including a conveyor, a mechanism for rotating the workpiece, and a probe.

U.S. Pat. No. 6,289,600 discloses a non-contact measuring device for determining the dimensions of a cylindrical object, such as a pipe.

U.S. Pat. No. 5,521,707 discloses a non-contact laser-based sensor guided by a precision mechanical system to scan a thread form producing a set of digitized images of the thread form.

WO 2009/130062 discloses a method and a device for the optical viewing of objects.

As described in U.S. Pat. No. 6,098,031, triangulation is the most commonly used 3-D imaging method and offers a good figure of merit for resolution and speed. U.S. Pat. Nos. 5,024,529 and 5,546,189 describe the use of triangulation-based systems for inspection of many industrial parts, including shiny surfaces like pins of a grid array. U.S. Pat. No. 5,617,209 shows a scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability.

U.S. Pat. No. 5,098,031 discloses a method and system for high-speed, 3-D imaging of microscopic targets. The system includes confocal and triangulation-based scanners or subsystems which provide data which is both acquired and processed under the control of a control algorithm to obtain information such as dimensional information about the microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The triangulation-based subsystem also includes a detector of electromagnetic radiation which is placed at a second location which is non-collinear with respect to the incident beam. Digital data is derived from signals produced by the detectors.

U.S. Pat. No. 5,815,275 discloses triangulation-based 3-D imaging using an angled scanning beam of radiant energy.

Published U.S. Patent Applications 2009/0103107 and 2009/0103112 disclose part inspection using a profile inspection subsystem and triangulation.

U.S. Pat. No. 4,547,674 discloses a method and apparatus for inspecting gear geometry via optical triangulation.

U.S. Pat. No. 4,970,401 discloses a non-contact triangulation probe system including a base plate and a first non-contact triangulation probe including a light source mounted on a first movable slide.

U.S. Pat. Nos. 5,168,458 and 5,170,306 disclose methods and systems for gauging threaded fasteners to obtain tri-lobular parameters.

Other U.S. patent documents related to the invention include: U.S. Pat. Nos. 4,315,688; 4,598,998; 4,644,394; 4,852,983; 4,906,098; 5,521,707; 5,608,530; 5,646,724; 5,291,272; 6,055,329; 4,983,043; 3,924,953; 5,164,995; 4,721,388; 4,969,746; 5,012,117; 7,684,054; 7,403,872; 7,633,635; 7,312,607, 7,777,900; 7,633,046; 7,633,634; 7,738,121; 7,755,754; 7,738,088; 7,796,278; 7,684,054; 8,054,460; 8,179,434 and U.S. published patent applications 2010/0245850, 2010/0201806, 2012/0293623; 2012/0105429; and 2012/0293789.

SUMMARY OF EXAMPLE EMBODIMENTS

An object of at least one embodiment of the present invention is to provide a high-speed, triangulation-based, 3-D method and system for inspecting manufactured parts and sorting the inspected parts at low cost and without rotating the part.

In carrying out the above object and other objects of at least one embodiment of the present invention, a high-speed triangulation-based, 3-D method of inspecting manufactured parts and sorting the inspected parts is provided. Each part has a length, a width, a part axis and an outer peripheral surface which extends 360° around the part. The method includes receiving a supply of parts, consecutively transferring the parts so that the parts move along a path which extends from the supply of parts and through a circumference imaging station and supporting a plurality of angularly-spaced, triangulation-based, sensor heads at the imaging station. Each of the sensor heads is configured to generate focused lines of radiation and to sense corresponding reflected lines of radiation. The method also includes delivering the focused lines onto a plurality of exterior side surfaces of the part during motion of the part relative to the focused lines to obtain corresponding arrays of reflected lines of radiation. The exterior side surfaces are angularly spaced about the axis of the part at the imaging station. The sensor heads simultaneously sense their corresponding arrays of reflected lines to obtain corresponding sets of 2-D profile signals. Each set of profile signals represents a 3-D view of one of the exterior side surfaces and the sets of 2-D profile signals represent a 360° panoramic composite 3-D view of the outer peripheral surface of the part. The method further includes processing the sets of 2-D profile signals of each part to identify parts having an unacceptable defect, directing parts identified as having an unacceptable defect to a defective part area and directing parts not identified as having an unacceptable defect to an acceptable part area.

The step of transferring may include the step of allowing each part to fall freely so that each part is unconfined and unobstructed during the step of delivering.

The part may have a radially extending surface, wherein the focused lines are angled with respect to the radially extending surface and wherein the 3-D view includes at least a portion of the radially extending surface.

Each part may be a cartridge case, wherein the step of processing determines at least one of a dent, a split, a perforation, a crack, a scratch, a wrinkle, a buckle, a bulge and a surface blemish located at the side surfaces of the case.

Each of the sensor heads may include at least one semiconductor laser.

The focused lines of radiation may be polarized laser lines of light.

Each part may be a threaded fastener wherein the step of processing determines a thread profile parameter.

The step of processing may identify a thread defect.

Further in carrying out the above object and other objects of at least one embodiment of the present invention, a high-speed, triangulation-based, 3-D system for inspecting manufactured parts and sorting the inspected parts is provided. Each of the parts has a length, a width, a part axis and an outer peripheral surface which extends 360° around the part. The system includes a source of parts and a transfer subsystem for consecutively transferring the parts from the source of parts so that the parts travel along a path which extends from the source of parts and through a circumference imaging station. The system also includes a plurality of angularly-spaced, triangulation-based, sensor heads. Each of the heads is configured to generate focused lines of radiation and to sense corresponding reflected lines of radiation. The heads are located at the imaging station to simultaneously deliver the focused lines onto a plurality of exterior side surfaces of the part during motion of the part relative to the focused lines to obtain corresponding arrays of reflected lines of radiation. The exterior side surfaces are angularly spaced about the axis of the part. The sensor heads simultaneously sense their corresponding arrays of reflected lines to obtain corresponding sets of 2-D profile signals. Each set of profile signals representing a 3-D view of one of the exterior side surfaces and the sets of 2-D profile signals representing at 360° panoramic composite 3-D view of the outer peripheral surface of the part. At least one processor processes the sets of 2-D profile signals to identify parts having an unacceptable defect. A mechanism including a part sorter directs parts identified as having an unacceptable defect to a defective part area and directs parts not identified as having an unacceptable defect to an acceptable part area. A system controller coupled to the at least one processor and the part sorter controls the sorting based on the inspecting.

The transfer subsystem may include a track adapted to consecutively receive parts to be inspected and enable the parts to slide there along by the force of gravity.

The part may have a radially extending surface, wherein the focused lines are angled with respect to the radially extending surface and wherein the 3-D view includes at least a portion of the radially extending surface.

Each part may be a cartridge case wherein the at least one processor determines at least one of a dent, a split, a perforation, a crack, a scratch, a wrinkle, a buckle, a bulge and a surface blemish located at the side surfaces of the case.

Each of the sensor heads may include at least one semiconductor laser.

The focused lines of radiation may be polarized laser lines of light.

Each part may be a threaded fastener wherein the at least one processor determines a thread profile parameter.

The at least one processor may identify a thread defect.

Other technical advantages will be readily apparent to one skilled in the art from the following figures, descriptions and claims. Moreover, while specific advantages have been enumerated, various embodiments may include all, some or none of the enumerated advantages.

BRIEF DESCRIPTION OF THE DRAWINGS

For a more complete understanding of the present invention, and for further features and advantages thereof, reference is made to the following description taken in conjunction with the accompanying drawings, in which.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

In general, and as described below, at least one embodiment of the present invention provides a high-speed, triangulation-based, 3-D method and system for inspecting manufactured parts at an imaging station and sorting the inspected parts. The parts, such as ammunition cases or threaded fasteners, have a length, a width, a part axis and an outer peripheral surface which extends 360° around the part.

Figure 1A:
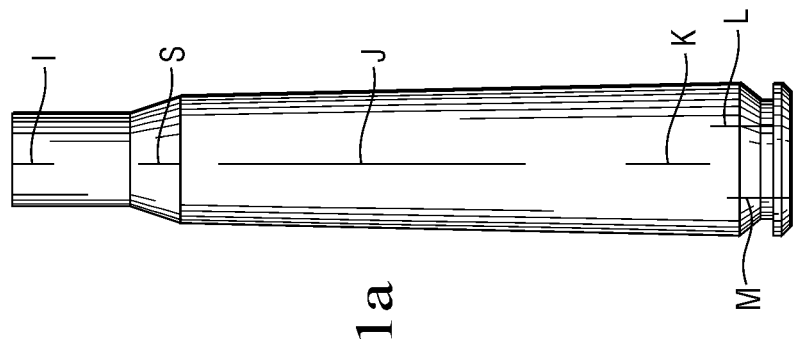
FIG. 1a is a side schematic view of a .50 caliber cartridge case.
Figure 1B:
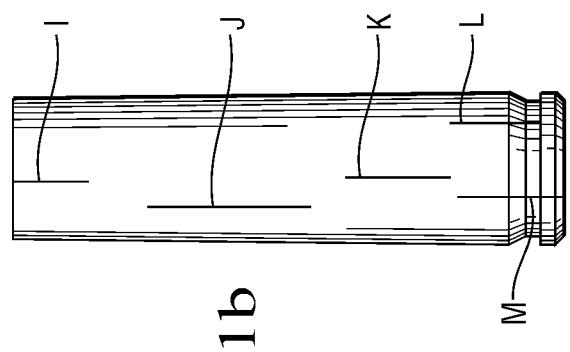
FIG. 1b is a side schematic view of a .30 caliber cartridge case.
Figure 1C:
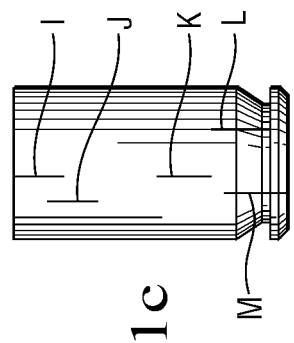
FIG. 1c is a side schematic view of a .45 caliber cartridge case.
Figure 2:
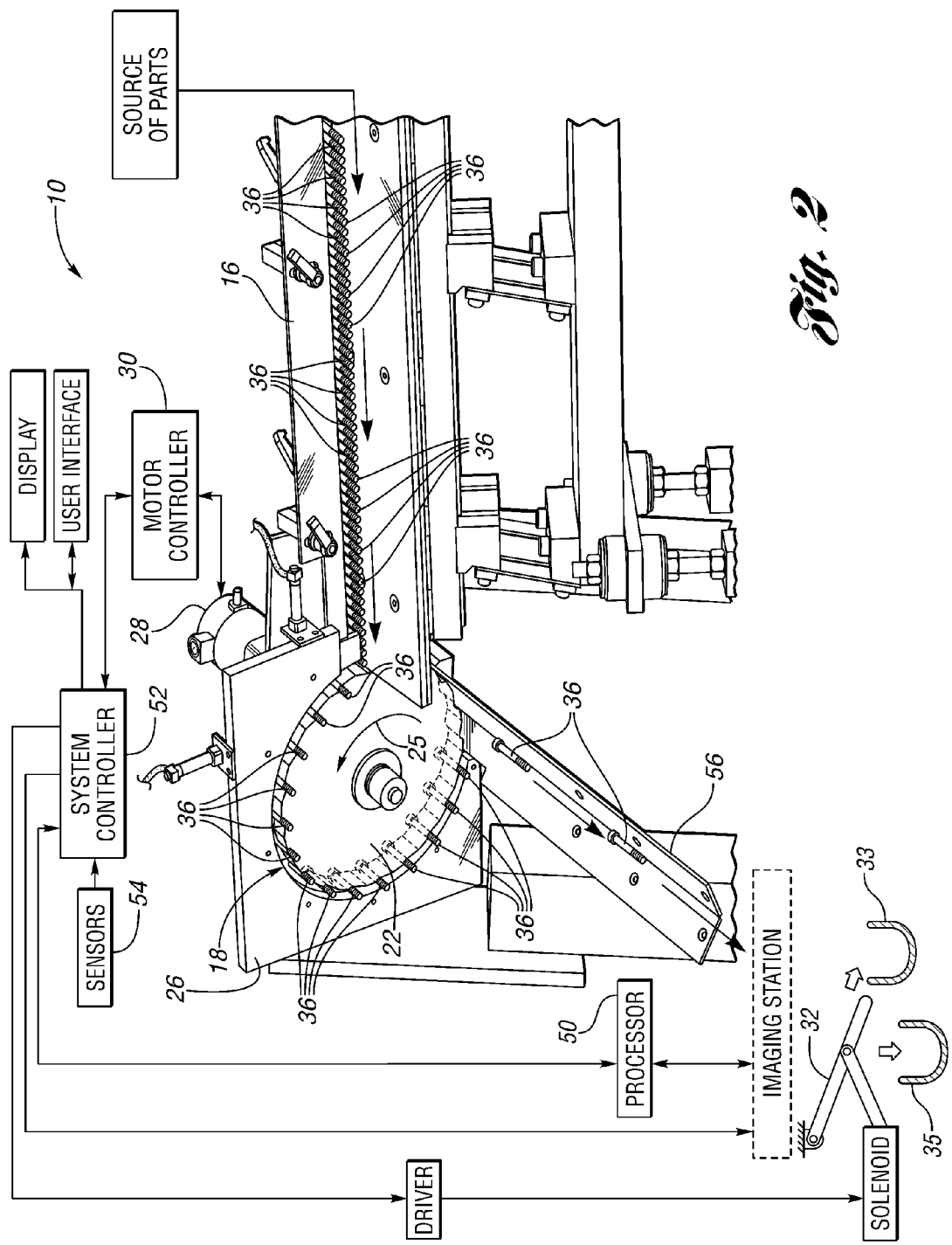
FIG. 2 is a schematic perspective view of an example embodiment of a system of the invention.

In general, one embodiment of the high-speed, triangulation-based, 3-D method and system of the present invention optically inspects manufactured parts such as cartridge cases or fasteners or bolts as illustrated in FIGS. 1 and 2. The inspected parts are then typically sorted based on the inspection. The system 10 is designed for the inspection of the outer peripheral surface of such cases or fasteners. However, the system 10 is also suitable for other small, mass-produced manufactured parts. The subsystems of the system 10 which may be used for part handling and delivery may vary widely from application to application depending on part size and shape, as well as what inspection is being conducted. The subsystems ultimately chosen for part handling and delivery have some bearing on the nature of the subsystem conducting the optical inspection.

Initially, parts, such as bolts 36 (FIG. 2), are placed into a source of parts such as a feeder bowl (not shown) having a scalloped rim. The bowl is supported on an adjustable frame structure. Tooling around the rim takes advantage of the asymmetrical mass distribution of the bolts 36 to feed the bolts 36 onto a downwardly sloped vibratory feeder conveyor or loader 16. Consequently, every bolt 36 which exits the bowl is received by the conveyor 16 and is oriented in the same direction as shown in FIG. 2. One or more vibrators (not shown) controlled by a vibrator controller (not shown) vibrate the bowl and the conveyor 16 to help move the bolts 36 in single file to a loading station. At the loading station the longitudinal axes of the bolts 36 are substantially parallel.

At the loading station, a part transfer subsystem, generally indicated at 18, of the high-speed, triangulation-based 3-D system 10 is provided to transfer the bolts 36 from the loading station, to an unloading station, where the now unsupported bolts 36 fall under the force of gravity. The subsystem 18 includes a transfer mechanism in the form of metering wheel 22 which is, preferably, made of an optically transparent plastic material such as acrylic. The wheel 22 has openings formed about its outer peripheral surface which are adapted to receive and support the bolts 36 at the loading station and to transfer the supported bolts 36 so that the bolts 36 travel along a first path indicated by an arrow 25 which extends from the loading station to the unloading station at which each bolt 36 has a predetermined position and orientation. The bolts 36 are supported on the wheel 22 during wheel rotation by a stationary guide 26. The wheel 22 is rotated by an electric motor 28 under the control of a motor controller 30 to rotate about its axis.

The system 10 also includes a system controller 52 which controls and coordinates the inspection of the bolts 36 with the transfer of the bolts 36 to control movement of the bolts 36 and the inspection of the bolts 33. The results of the processing by at least one processor such as a signal processor 50 are output to the system controller 52 which controls the system 10 based on the results of the optical inspection. Sensors 54 provide various timing or position signals to the controller 52 to help control the system 10. For example, one type of sensor may signal the controller 52 when the bolts 36 are located at or near the imaging station in the system 10 so that sensor heads, generally indicated at 44 in FIGS. 2-5, can be controlled by the controller 52 to take "pictures" of the bolts 36 at the imaging station.

The system 10 may also include a display and a user interface to permit two-way user interaction with the system 10.

The bolts 36 may be dropped onto a track 56 which may take the form of an AMPCO 18 oriented at a 35° angle. As the bolts 36 slide down and exit the track 56, they pass through the imaging station to be inspected one at a time. Bolts 36 which pass the inspection may be actively accepted by a part diverter or flipper 32 located a few inches below the bottom end of the track 56. The solenoid-actuated flipper 32 actively accepts those parts which have passed the above inspection into an acceptable part receive area 33. The flipper 32 rests by default in its reject position so that parts will not be falsely accepted in the unlikely event of a hardware or software malfunction.

Figure 3:
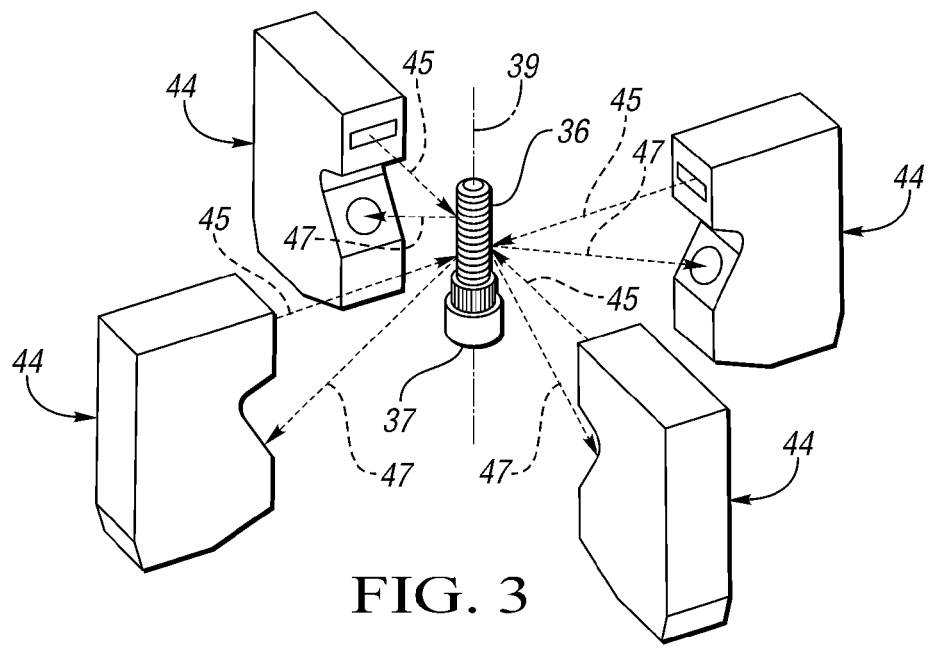
FIG. 3 is a schematic perspective view of a threaded fastener and a plurality of angularly-spaced, triangulation-based, sensor heads at an imaging station.
Figure 4:
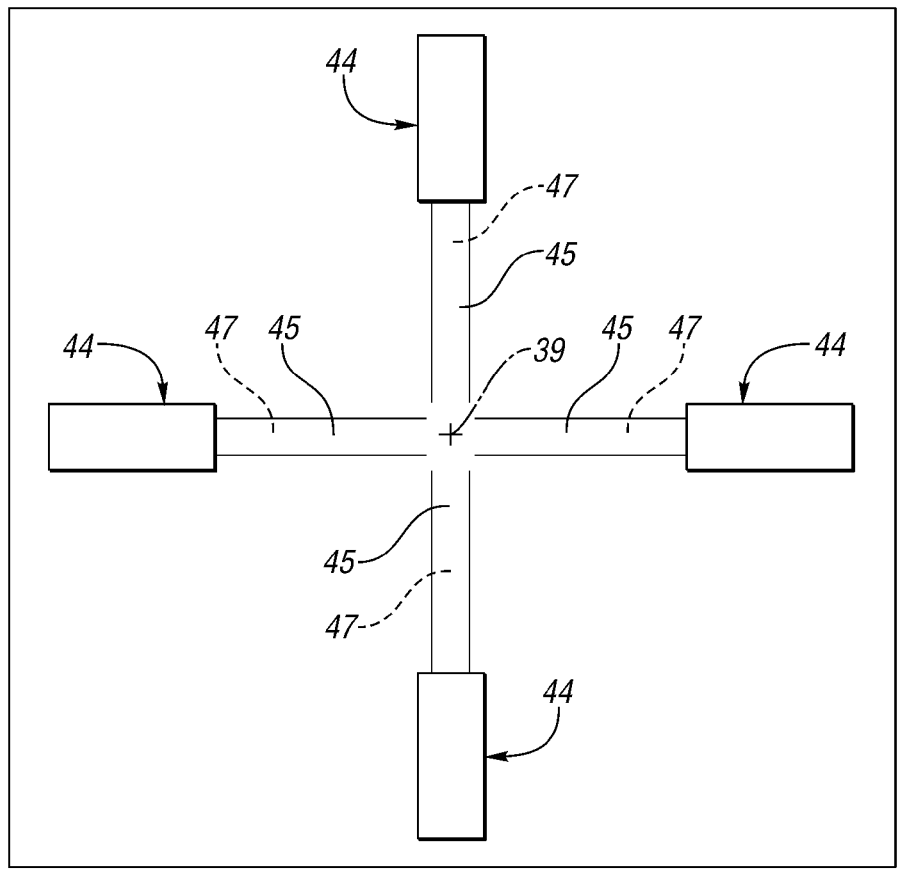
FIG. 4 is a top schematic block diagram view of a plurality of angularly-spaced sensor heads of at least one embodiment of the invention.
Figure 5:
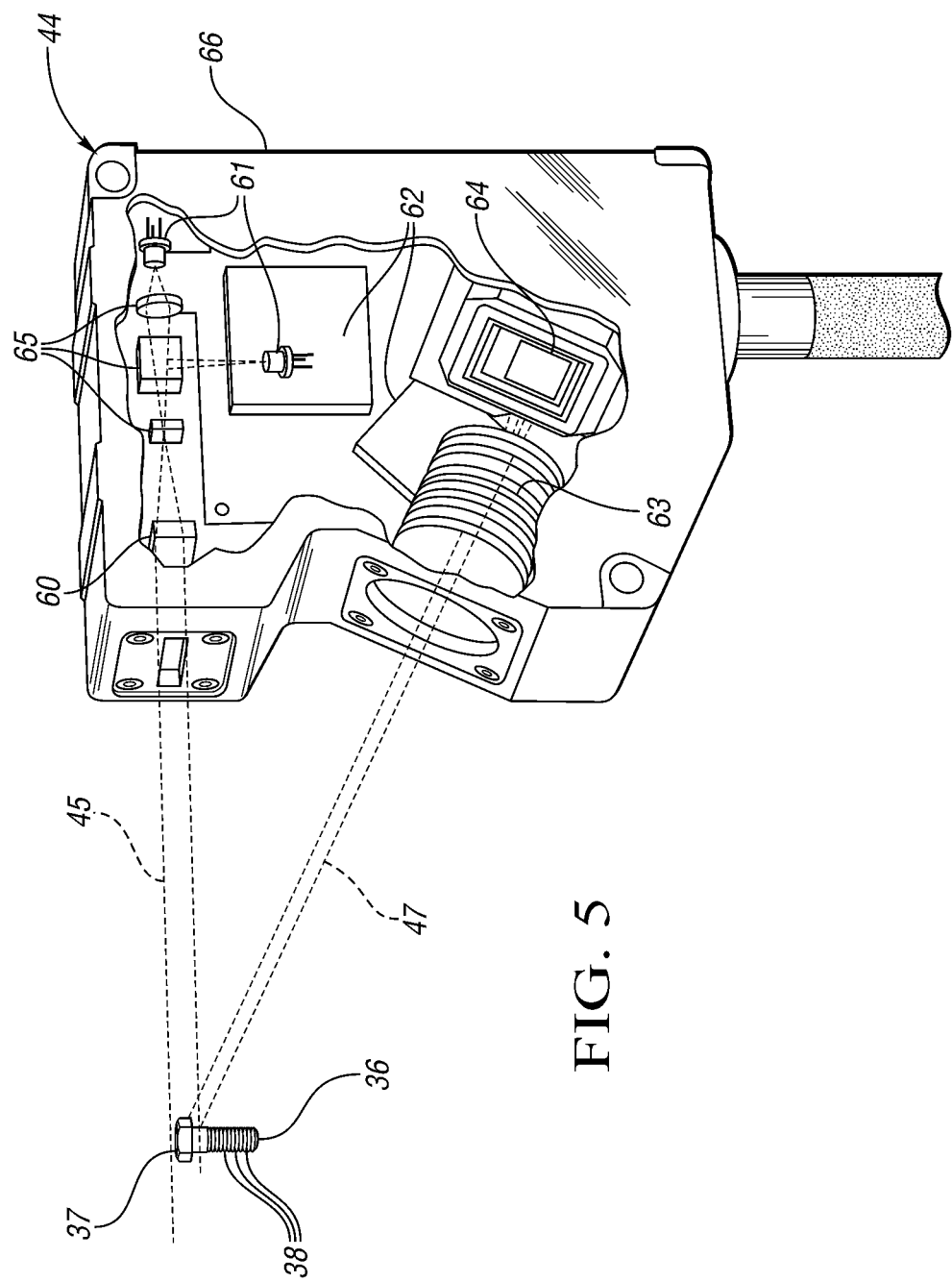
FIG. 5 is a schematic perspective view (partially broken away) of the various components of a sensor head of a preferred embodiment of the system.

Generally, and as shown in FIGS. 3 and 4, a plurality of angularly-spaced, triangulation-based sensor heads 44 are supported and mounted within the imaging station. The sensor heads 44 simultaneously illuminate a plurality of exterior side surfaces of each bolt 36 with focused planes or lines 45 of radiation to obtain corresponding reflected lines 47 when the part 36 is in the imaging station as indicated by the sensors 54 (FIG. 2). The exterior side surfaces are angularly spaced about an axis 39 of the part 36. The sensor heads 44 simultaneously sense their corresponding reflected lines 47 to obtain corresponding 2-D profile signals.

Figure 7:
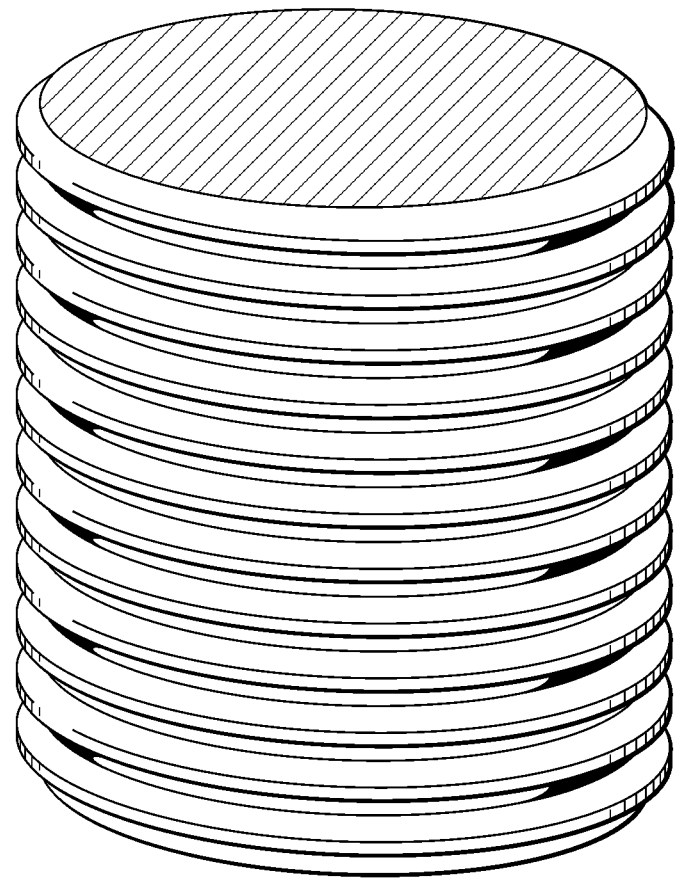
FIG. 7 is a schematic, perspective view, in cross section, of a continuous, seamless, 360 degree panoramic composite 3-D image or view formed by processing sets of 2-D profile signals.

As the parts 36 fall through the imaging station, corresponding sets of 2-D profile signals are generated by the sensor heads 44. At least one processor (FIG. 2) processes the sets of 2-D profile signals to obtain a 360° panoramic composite 3-D view of the outer peripheral surface of the part 36. The 3-D view may be continuous and seamless as shown in FIG. 7 by "stitching" the various views together.

The system controller 55 provides control signals based on the signals from the sensors 54. The control signals are utilized to control the sensor heads 44 which preferably have inputs which allow precise control over the position of 2-D profile signals samples.

The bolts 36 may be undercut to have a radially extending surface wherein the focused lines 45 are angled with respect to the radially extending surface. The 3-D view may include at least a portion of the radially extending surface in this example.

The at least one processor may process the sets of 2-D profile signals to identify a defective part as described in greater detail hereinbelow.

The at least one processor may process the sets of 2-D profile signals to obtain a measurement of the part as also described in greater detail hereinbelow.

Each of the sensor heads 44 may comprise a high-speed, 2D/3D laser scanner (LJ-V7000 series) available from Keyence Corporation of Japan. Such a sensor head from Keyence generates a laser beam that has been expanded into a line and is reflected from the surface of the part. This reflected line of light is formed on a HSE3-CMOS sensor and by detecting changes in the position and shape of the reflection, it is possible to measure the position of various points along the surface of the part.

Such a sensor head 44 typically includes (FIG. 5) a cylindrical lens 60, at least one and preferably two semiconductor laser diodes 61, a GP64-Processor 62, a 2D Ernostar lens 63 and a HSE3-CMOS Sensor 64. Preferably, the laser diodes 61 emit "blue" light beams which are polarized and combined by optical elements or components 65 to form the line of laser light 45.

Preferably, the beams from the pair of blue laser diodes 61 are combined such that the transmitted beam is polarized in both X and Y axes. The captured images at the sensor 64 in both polarizations are used to generate a resulting 2-D profile signal wherein stray reflections are cancelled.

A comparison of such sensor heads 44 with 3-D measurement cameras reveal the following:

1. Easy Installation

When using a 3D camera, the laser light source and receiver (camera) are independent of each other, greatly complicating on-site installation and adjustment. With such sensor heads 44, the laser light source and receiver are contained in a single body or enclosure 66, making transmitter-to-receiver mounting adjustment unnecessary. This also ensures that the transmitter and receiver maintain this alignment regardless of machine use.

2. No Linearization Required

When using a 3D camera, the height of individual pixels and pixel pitch vary due to the relative positions of the laser light source and the receiver, requiring on-site linearization following installation. With such sensor heads 44, the output data is pre-linearized by the on-board controller (not shown) of the sensor head 44 without the need for additional post-processing.

3. Out of the Box Traceability

Because each such sensor head 44 is not a machine vision camera, but a traceable measurement device, traceability and calibration documentation is available out of the box. All such devices are factory calibrated to international traceability standards and compliance documentation is readily available.

The sensor heads 44 and the at least one processor can extract serrations, knurls, twelve point aerospace or non-symmetric features of parts like D-head or T-head bolts etc. The operator may tell the system controller (FIG. 2) via a display and user interface where the interesting parameters are located on the part axis (height of the part). Then, the software tools extract and measure features from the images and resulting 2-D profile signals created by the sensed reflected lines of radiation.

The 2-D profile signals may be pre-processed by the processor 62 and then processed by the at least one processor 50 under system control to obtain a 360 degree panoramic composite view or image which is used by the processor 50 to determine at least one of a dent, a split, a perforation, a crack, a scratch, a wrinkle, a buckle, a bulge, and a surface blemish located at the side surfaces of the part where the part is an ammunition case.

The system 10 is an integrated system designed to fully inspect and measure parts from their sides without any need for part rotation at the imaging station. The system 10 can inspect parts which are supported such as a track which has a slit formed therein to allow a 360° unobstructed view of the part 36.

Three or possibly four (as described herein), partially overlapped, views of the part are simultaneously provided. Each optical path is designed so that the displacement angle between the views is almost exactly 90° (or 120° if three sensor heads 44 are provided). This optical layout ensures complete coverage of the case's (or fastener's) lateral surfaces. The optical path is the same for all four viewpoints. Furthermore, such imaging makes the system 10 relatively insensitive to part decentering and therefore suitable for measurement applications. The system 10 provides a solution for inspecting parts, such as cases or fasteners, whose features would be hidden when looked at from the top and for all those applications where a part must be inspected or measured from different sides without part rotation.

FIG. 7 is a schematic, perspective view, in cross section, of a continuous, seamless, 360 degree panoramic composite 3-D image or view formed by processing a plurality of separate sets of 2-D profile signals. Each "curved" 3-D view may be "stitched" or joined together by a conventional image processing algorithm to form the 3-D view.

Figure 11:
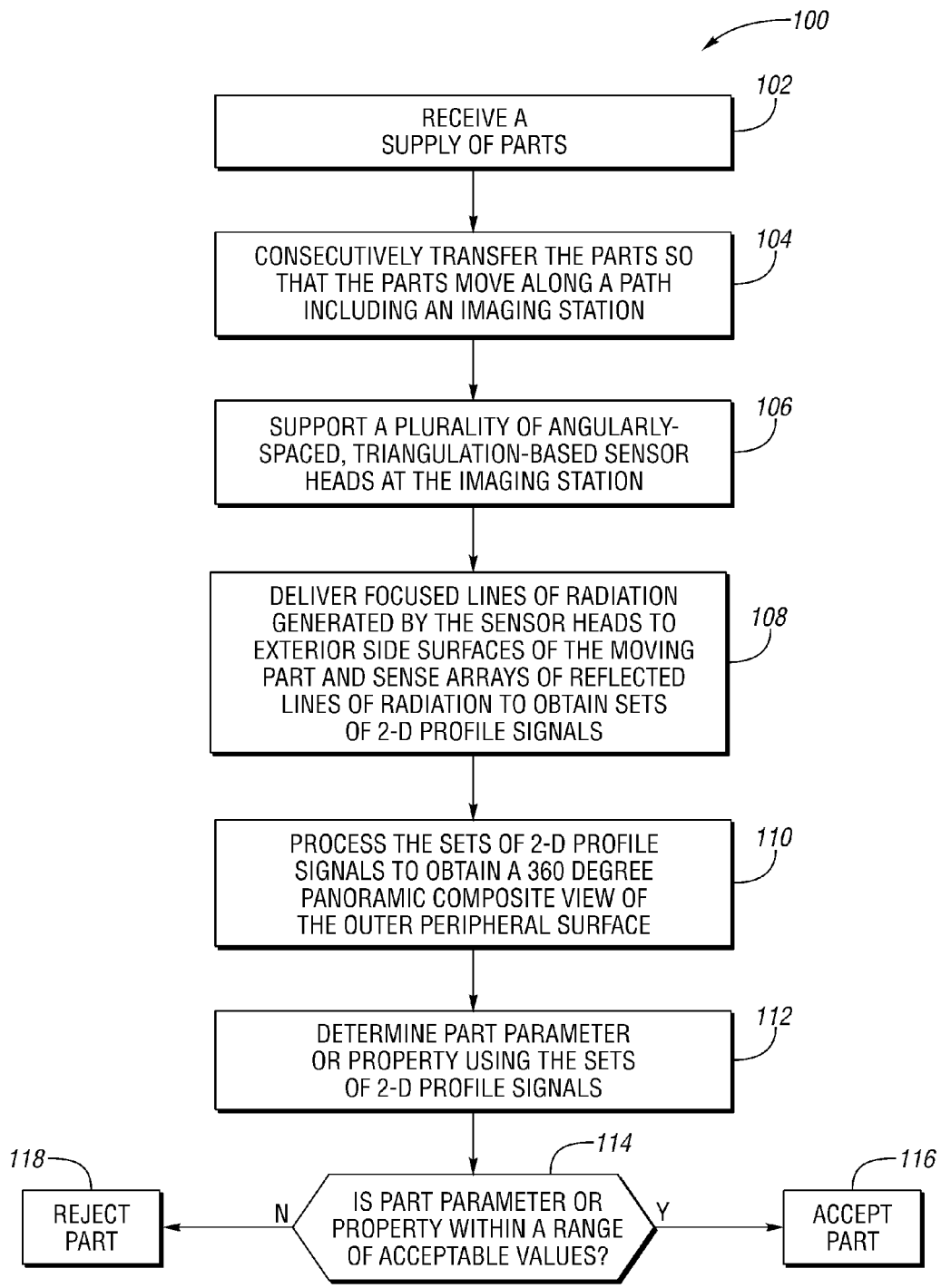
FIG. 11 is a block diagram flow chart illustrating a high-speed, triangulation-based, 3-D method of optically inspecting and sorting the inspected parts in accordance with at least one embodiment of the invention.

FIG. 11 is a detailed block diagram flow chart describing a method of at least one embodiment of the present invention, generally indicated at 100, as follows:

1. Receive a supply of parts such as bolts 36 or ammunition cases as shown in FIGS. 1*a*-1*c* (block 102);

2. Consecutively transfer the parts so that the parts move along a path including an imaging station (block 104);

3. Support a plurality of angular-spaced, triangulation-based sensor heads 44 at the imaging station (block 106);

4. Deliver focused lines of radiation generated by the sensor heads 44 to exterior side surfaces of the moving part and sense arrays of the reflected lines of radiation to obtain sets of 2-D profile signals (block 108);

5. Process the sets of 2-D profile signals to obtain 360 degree panoramic composite view of the outer peripheral surface of the part (block 110);

6. Determine part parameter or property using the sets of 2-D profile signals (block 112);

7. Is part parameter or property within a range of acceptable values? (block 114);

8. If block 114 is "yes" accept part (block 116); and

9. If block 114 is "no" reject part as being defective (block 118).

Signal Processor for the Detection of Surface Defects on Small Manufactured Parts This vision system 10 is especially designed for the inspection of relatively small manufactured parts such as threaded fasteners and small and medium caliber ammunition. The processing of images and/or signals of the cartridge cases to detect defective cases is generally described in issued U.S. Pat. No. 7,403,872 as described in the following Appendix with regard to a composite image.

APPENDIX

Dent Detection

The detection of dents relies on the alteration of the angle of reflected light caused by a surface deformation on the inspected part. Light which is incident on a surface dent will reflect along a different axis than light which is incident on a non-deformed section of circumference.

There are generally two ways to detect dents using this theory. One option is to orient the light source so that light reflected off the part exterior is aimed directly into the sensor head aperture. Light which reflects off a dented region will not reflect bright background. Alternatively, the light source can be positioned with a shallower angle to the part. This will result in a low background illumination level with dents appearing as well deemed origin spots on the image.

The vision system detects dents on parts with multiple tapered sections. In particular, a bright background is created in highly tapered regions (with dents appearing as dark spots) while a dim background is created in flatter regions (with dents appearing as bright spots).

Perforation Detection

Detecting perforations uses both of the principles outlined above. The task is much simpler however, as the region containing the defect is completely non-reflective. Therefore, perforations are visible as dark spots on surfaces illuminated by either shallow or steep angle illumination.

Software

Because the part is essentially at a predefined location and orientation when the images are acquired, the software need not auto-locate the part and identify regions of interest using preset visual clues.

Defect detection in each region of interest is typically conducted by first running several image processing algorithms and then analyzing the resultant pixel brightness values. Groups of pixels whose brightness values exceed a preset threshold are flagged as a "bright defect," while groups of pixels whose brightness values lie below a preset threshold are flagged as a "dark defect." Different image processing techniques and threshold values are often needed to inspect for bright and dark defects, even within the same part region.

Part Location

Previously locating the part in the composite image may be accomplished by running a series of linear edge detection algorithms. This algorithm uses variable threshold, smoothing and size settings to determine the boundary between a light and dark region along a defined line. These three variables are not generally available to the user, but are hard-coded into the software, as the only time they will generally need to change is in the event of large scale lighting adjustments.

The software first uses the above edge detection algorithm to find the back (left) end of the part in the image.

Once the left edge of the part has been located, the software runs four more edge searches along the top and bottom edges of the part.

Once the top and bottom edges of the part have been located, the midpoints of the edge pairs are calculated and joined in order to find the centerline.

The centerline search is then performed again, but rather than conducting the linear edge detections in the vertical direction, they are conducted perpendicular to the newly found centerline. This iteration reduces the small angle error associated with any potential misalignment of the part in the field of view.

A new centerline found using the results of the repeated top and bottom edge search.

Finally, the left edge is again located, this time along the new centerline. This action locates the very center of the left-hand edge of the part.

Part Regions

Figure 8:
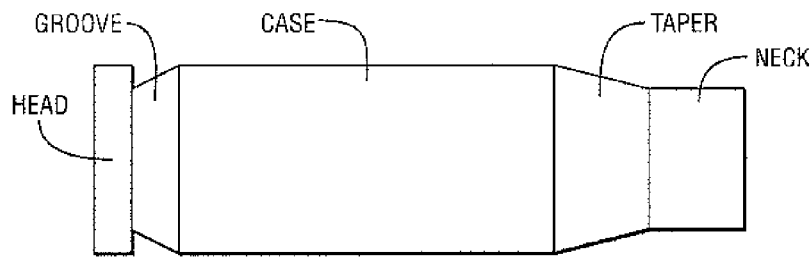
FIG. 8 is a schematic view wherein a framework in the illustrated figure is applied to a part such as a cartridge case once it has been located.

Once the part has been located in the composite image, a framework of part regions is defined using a hard-coded model of the anticipated part shape. In the case of ammunition, the regions defined by the framework include head, extractor groove, case, taper, and neck. Each of these regions can be varied in length and width through the user interface in order to adapt the software to varying case sizes. Note that although regions can be adjusted in size, they cannot have their bulk shape changed. A checkbox allows the taper and neck regions to be removed in order to inspect pistol cases (which do not have a taper). The size of the region framework as well as the state of the Taper/No-Taper checkbox is saved in the part profile. FIG. 8 shows the definition of the various regions on the part.

Figure 9:
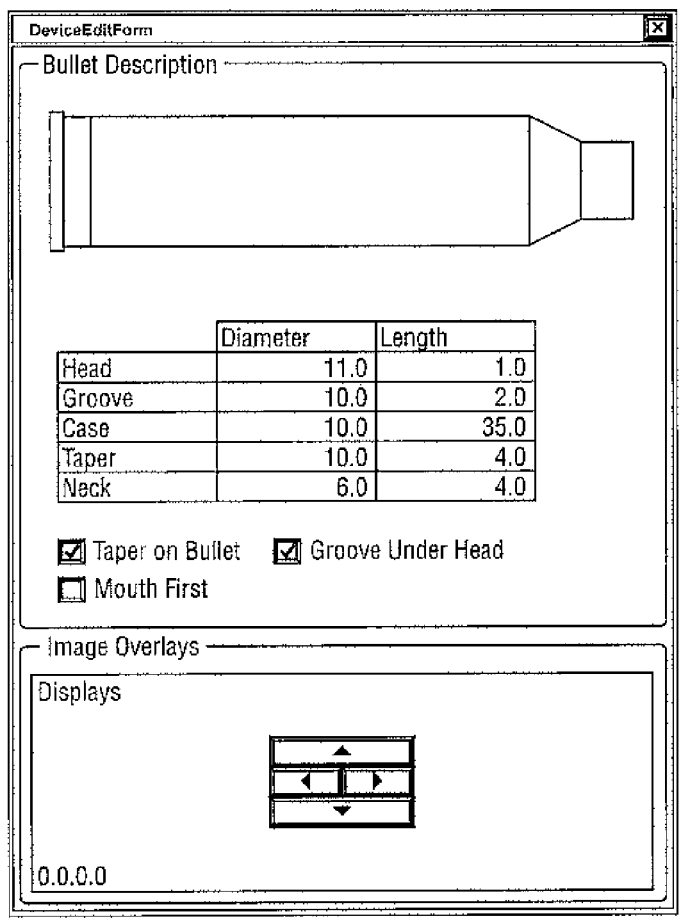
FIG. 9 is a schematic view of a screen shot which describes a cartridge case or bullet to be inspected.

This region definition is shown in screenshot of FIG. 9. Note how the diameter of the groove has been set to be the same as the diameter of the case, resulting in a rectangular groove profile, rather than the trapezoid that is more frequently used.

Defect Search

Figure 10:
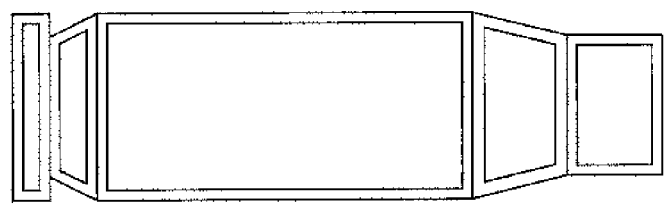
FIG. 10 is a schematic view similar to the view of FIG. 8 wherein buffers are applied once the case regions has been identified.

Once the case regions have been defined, a buffer distance is applied to the inside edges of each region. These buffered regions define the area within which the defect searches will be conducted. By buffering the inspection regions, edge anomalies and non-ideal lighting frequently found near the boundaries are ignored. The size of the buffers can be independently adjusted for each region as part of the standard user interface and is saved in the part profile. This concept is demonstrated in FIG. 10.

There are two general defect detection algorithms that can be conducted in each region. These two algorithms are closely tied to the detection of dents and perforations respectively as discussed above in the lighting section. More generally however, they correspond to the recognition of a group of dark pixels on a bright background or a group of bright pixels on a dark background.

Although there are only two defect detection algorithms used across all the regions on the part, the parameters associated with the algorithm can be modified from region to region. Additionally, the detection of dark and/or bright defects can be disabled for specific regions. This information is saved in the part profile.

Dark Defects

The detection of dark defects is a 6 step process.

1. Logarithm: Each, pixel brightness value (0-255) is replaced with the log of its brightness value. This serves to expand the brightness values of darker regions while compressing the values of brighter regions, thereby making it easier to find dark defects on a dim background.

2. Sobel Magnitude Operator: The Sobel Operator is the derivative of the image. Therefore, the Sobel Magnitude is shown below:

$$S_M = \sqrt{\left(\frac{\partial f}{\partial x}\right)^2 + \left(\frac{\partial f}{\partial y}\right)^2}$$

although it is frequently approximated as the following:

$$S_M = \frac{\frac{\partial f}{\partial x} + \frac{\partial f}{\partial y}}{2}$$

The Sobel Magnitude Operator highlights pixels according to the difference between their brightness and the brightness of their neighbors. Since this operator is performed after the Logarithm filter applied in step 1, the resulting image will emphasize dark pockets on an otherwise dim background. After the Sobel Magnitude Operator is applied, the image will contain a number of bright 'rings' around the identified dark defects.

3. Invert Original Image: The original image captured by the camera is inverted so that bright pixels appear dark and dark pixels appear bright. This results in an image with dark defect areas appearing as bright spots.

4. Multiplication: the image obtained after step 2 is multiplied with the image obtained after step 3. Multiplication of two images like this is functionally equivalent to performing an AND operation on them. Only pixels which appear bright in the resultant image. In this case, the multiplication of these two images will result in the highlighting of the rings found in step two, but only if these rings surround a dark spot.

5. Threshold: All pixels with a brightness below a specified value are set to OFF while all pixels greater than or equal to the specified value are set to ON.

6. Fill in Holes: The image obtained after the completion of steps 1-5 appears as a series of ON-pixel rings. The final step is to fill in all enclosed contours with ON pixels.

After completing these steps, the resultant image should consist of a pixels corresponding to potential defects. These bright blobs are superimposed on areas that originally contained dark defects.

Bright Defects

The detection of bright defects is a two-step process.

1. Threshold: A pixel brightness threshold filter may be applied to pick out all saturated pixels (greyscale255). A user-definable threshold may be provided so values lower than 255 can be detected.

2. Count Filter: A count filter is a technique for filtering small pixel noise. A size parameter is set (2, 3, 4, etc) and a square box is constructed whose sides are this number of pixels in length. Therefore, if the size parameter is set to 3, the box will be 3 pixels by 3 pixels. This box is then centered on every pixel picked out by the threshold filter applied in step 1. The filter then counts the number of additional pixels contained within the box which have been flagged by the threshold filter and verifies that there is at least one other saturated pixel present. Any pixel which fails this test has its brightness set to 0. The effect of this filter operation is to blank out isolated noise pixels.

Once these two steps have been completed, the resultant binary image will consist of ON pixels corresponding to potential defects. Furthermore, any "speckling" type noise in the original image which would have results in an ON pixel will have been eliminated leaving only those pixels which are in close proximity to other pixels which are ON.

Pixel Count

After bright and/or dark defect detection algorithms have been run in a given region, the resultant processed images are binary. These two images are then OR'ed together. This results in a single image with both bright and dark defects.

The software now counts the number of ON pixels in each detected defect. Finally, the part will be flagged as defective if either the quantity of defect pixels within a given connected region is above a user-defined threshold, or if the total quantity of defect pixels across the entire part is above a user-defined threshold.

Thread Signal/Data Processing

Introduction

Figure 6:
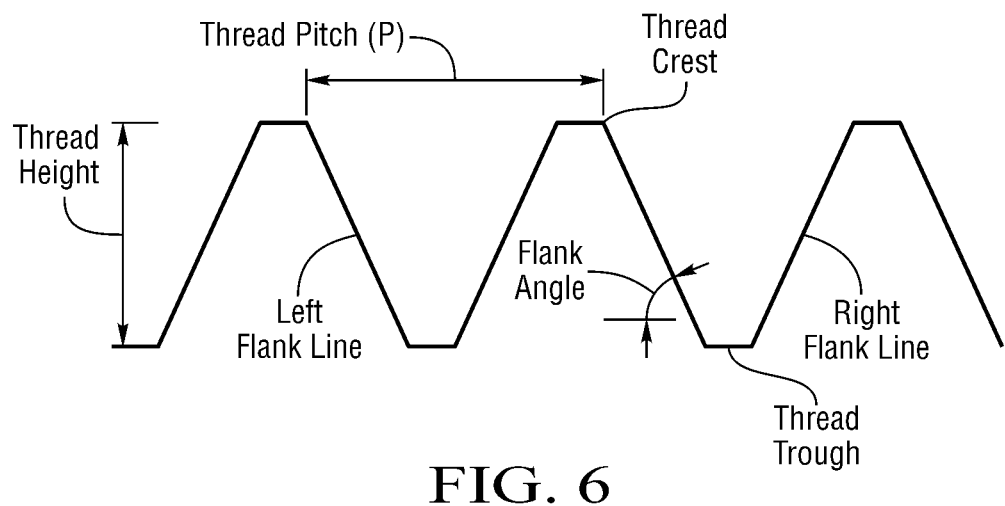
FIG. 6 is a graph wherein a thread profile and some of its parameters are illustrated.

What follows is a description of a thread parameter estimation process. This process which is described in general in published U.S. patent application 2010/0238435 provides one embodiment of a standard thread measurement "feature" in the method and system of the invention and as shown in FIG. 6.

Thread Signal Processing

Thread signal processing is the process of estimating the following thread parameters.
1) pitch
2) major diameter
3) minor diameter
4) functional diameter
5) lead deviation
6) pitch diameter As the thread signal processing proceeds, a number of intermediate data products are produced in early processing stages that are further analyzed in later stages. These include:
rough pos/neg crossing locations
rough crest locations
wire position search intervals
left/right flank lines
wire positions
precise crest/root locations
3-crest average/median measurements of major diameter, minor diameter, pitch diameter
3-D crest cylinder axis
wire position projections on the 3-D crest cylinder axis
3-D crest cylinder diameter
3-D crest root-mean-square distance between crest data and fit.

These intermediate data products are analyzed to produce final estimates of the thread parameters. For example major diameter is estimated as twice the radius of the 3-D crest cylinder. The 3-D crest cylinder axis then depends on the precise crest/root locations. The crest/root locations then depend on the search intervals based on rough crest locations and pos/neg crossings, and on data from the original calibrated part data.

Processing Restrictions

Inspection Region

The thread processing occurs between position limits called an inspection region. In template editor, the user specifies the inspection region via a user interface (FIG. 2) by manipulating the upper and lower stage position limits, overlaid on an image of the part.

These limits utilize the calibrated sensor position so that measurements by are aligned to the approximately similar physical positions on the part.

The estimation of thread parameters is specified to be an average estimate over all the data within which the inspection region. In practice, some of the intermediate data products are estimated outside of the inspection region in order to allow estimation of all thread parameters within the full region. For example, a wire position within the inspection region may require a thread crest outside the inspection region.

Measurement Assumption for the Inspection Region

The following requirements guide the user's placement of the inspection region on the image of the part.

The first assumption is that the thread parameters be constant throughout the inspection region. This enables the software to average the estimates from different positions within the inspection region and not be concerned with partitioning or segmenting the data into different regions for special processing.

This requirement excludes the following types of data from the inspection region:
the beginning or end of a threaded region, with thread crests less than full height.
a threaded region with a taper.
a threaded region with a notch or extensive damage.

A second assumption is that the inspection region contains at least 4-6 thread pitches. This amount of data is required to construct several of the intermediate data products with the required accuracy.

A third assumption is that the thread be manufactured with a 60-degree flank angle. Thread processing implicitly utilizes this parameter in several places. One of the most direct usages is the conversion of lead deviation into functional diameter.

A fourth assumption is that the thread has a cylindrical cross section. Non-cylindrical threads would require the 3-D peak cylinder to be suitably generalized. Incorrect fit to a non-cylindrical cross section would lead to incorrect lead deviation measures.

A fifth assumption is that the thread has a single helix.

Measurement of the following threaded fasteners are provided:

non-standard thread types, especially self-tapping screws, small threaded regions with 2 or 3 pitches.

Taptite trilobe threaded regions.

Rough Crossings

The thread model describes herein below is a sampled representation of one thread profile, for exactly one pitch. Thread model starts at the midpoint of a rising thread flank and ends one pitch later.

Using a correlation detector, the thread model is matched to data within the inspection regions producing thresholded detections within the inspection region, that are called crossings.

"Refinements" noted herein may make the crossings more accurate. The refinements also separate the crossings into positive crossings and negative crossings. FIG. 6 illustrates selected concepts of a thread form. The thread model is a lateral sequence of points that represent a best estimate of the outline of one cycle of the thread form.

Rough Crest and Root Positions

A crest/root detector extracts rough crest and root positions between the matched adjacent pairs of positive and negative crossings.

Pitch Estimate

A pitch estimate is required for step set gage wire diameter. The estimate is required to be accurate enough to unambiguously select a unique gage wire from the set appropriate for the measurement. The current process utilizes a two-stage process.

This process may be simplified as described herein.

First Estimate.

Crossing data is analyzed and averaged over all sensors to create a thread pitch estimate, the "crossing pitch."

Second Pitch Estimate

The steps set wire gage diameter, wire position search intervals, measure flank lines and measure 3-point diameters noted herein below are completed in a first iteration. Then the wire positions are averaged over all sensors and positions to compute a pitch estimate.

Set Gage Wire Diameter

Gage wires are utilized in physical thread measurements of pitch diameter in the prior art. Two wires are placed in adjacent threads on one side of the part, and a single wire is placed on the other side of the part. A micrometer measures the distance between the reference line established by the two adjacent gage wires and the reference point established by the other gage wire. A tabulated correction formula converts the micrometer distance to an estimate of the pitch diameter.

Gage wire sizes are thus selected prior to the thread measurement. To do this one estimates the thread pitch as previously described and then one selects the closest gage wire in a set to the pitch estimate. The gage wire set utilized is the one appropriate to the type of measurement; currently there is one set for the metric coarse thread sequence, and another for a similar English thread set. The gage wire sets are chosen at part template edit time by making a selection in a pull down list.

Wire Position Search Intervals

One places "virtual" gage wires onto the calibrated sensor data throughout the inspection region. In order to place the "virtual" gage wires we must identify search intervals for each wire to be located.

A requirement of the following processing steps is that the wire positions in the inspection region have no gaps. Another requirement is that a wire position search interval consist of two valid thread crests, one valid thread root between the two thread crests, and valid positive/negative crossings between the crest/root pairs.

One then searches the set of positive/negative crossings and crest/root positions for the set of wire position search intervals to analyze. The result of intervals, one set per sensor.

Measure Flank Lines

For a left flank all data is analyzed between the rough positions of the left crest and the central root. One then determines the height limits of a flank line data extraction region that covers 70% (a configurable parameter) of the height interval between left crest and central root. This data is extracted into a data set and fit to a line, becoming the left flank line.

The procedure avoids the non-linear regions near the left crest and central root. In addition, a "flank line valid" flag is computed, based on the RMS distance between the left flank line and the data within the left flank line data extraction region. If the RMS distance between the flank line and the data points in the flank line data extraction interval is larger than 10 μm per point (a configurable parameter), then the flag is set to invalid.

The process is repeated for the right flank line and then for all wire position search intervals.

Measure Wire Positions

The wire positions are calculated, given the left and right flank lines and the wire size. The virtual wire is tangent to each flank line and the resulting position is calculated with a simple geometric formula.

The position has a valid flag that is true when both flank lines are valid, and false otherwise.

Measure 3-Point Diameters

The 3-point technique is a method to measure the minor, major, and pitch diameters without explicitly utilizing 3-D information.

For example, consider the major diameter. It is defined as the diameter of a cylinder that contains all the inspection region's thread crests.

In this method, the top of a thread crest in calibrated sensor coordinates forms an elementary measurement. The elementary measurements are combined into triplets for further analysis.

Two adjacent thread crest positions are combined with the thread crest position that is closest to the average position of crests. The two crests form a reference line. Then the distance from the reference line to the crest is computed. This is the 3 crest distance for that crest triplet.

In this manner, the 3-crest distances from all adjacent crest triplets are computed. The 3-crest distances are all added to a data vector. The 3-crest diameter measurement is either the average or the median of all the 3-crest distances within the 3-crest data vector.

3-Point Minor Diameter

The 3-point minor diameter computes 3-point distances using precise root locations in the sensor data. The 3-point minor diameter is the average of the 3-point distance vector.

3-Point Major Diameter

The 3-point major diameter computes 3-crest distances using precise crest locations in the sensor data. The 3-point major diameter is the median of the 3-point distance vector.

3-Point Wire Pitch Diameter

The 3-point pitch diameter computes 3-point distances using the wire positions computed in the sensor data. The 3-point wire pitch diameter is the median of the 3-point wire pitch diameter.

Measure 3-D Crest Cylinder

The measured thread crest position data is analyzed to obtain a 3-D cylinder with least squares methods. The 3-D crest cylinder fit has several output parameters of interest.

the RMS distance between the crest position data and the fitted shape.

the 3-D location of the cylinder's central axis.

the radius of the cylinder

Project Wire Positions onto 3-D Crest Cylinder Axis

Measured wire positions can be combined with the 3-D location of the 3-D crest cylinder's central axis. An imaginary disk, perpendicular to the cylinder axis that goes through the measured wire position marks a position on the 3-D crest cylinder axis.

A data set consisting of the projections of all sensor wire positions is constructed.

The output intermediate data is a vector, sorted from minimum to maximum sensor stage position of the projected wire positions.

Thread Parameter Estimation

Thread parameter estimation utilizes the intermediate data products and may also correct them based on a model of the measurement, prior to producing a final thread parameter estimate.

Wire Pitch

Thread pitch is estimated from the wire center intermediate data. For each sensor data set the adjacent pairs of wire positions are used to calculate an adjacent wire pitch, one per adjacent wire positions. For all lasers, each wire pitch is added to a wire pitch vector.

The wire pitch estimate is the median of the elements in the wire pitch vector.

Major Diameter

Thread major diameter is typically reported as the diameter of the 3-D crest cylinder.

If the 3-D crest cylinder fit was unsuccessful, the major diameter is estimated in a different way, detailed below. The cylinder fit can fail due to several factors listed here:

part inclined at too great an angle with respect to the stage axis.

thread crest positions do not fit a cylinder, the RMS fit-to-data distance is too large.

When the cylinder fit fails the major diameter is estimated from the 3-point major diameter data. This case is special because a previous condition (cylinder fit) has already failed. In practice, the cylinder fit most often failed when the threaded region was too short or the inspection extended beyond the end of the threaded region.

Because of this bias a simple median of the 3-point major diameter data would typically be too low, most of the good 3-point data was concentrated at the highest measurements. In this case the major diameter estimate is the value such that 20% of the 3-point data is higher and 80% of the 3-point data is lower.

Calibration Correction

Major diameter is also corrected by a final end-to-end calibration of the total system. The reported major diameter is often two low, with bias ranging from −20 μm to 0.

After diameter calibration the system is exposed to a set of measured thread plug gages. One then plots their major diameter bias as a function of diameter and fit a simple segmented line to the bias results. These bias fits then are entered into the system configuration file and are used to correct the measured major diameter with the measured bias.

Minor Diameter

Thread minor diameter is estimated with the 3-point minor diameter distance vector. The minor diameter value is the average of the elements in the distance vector.

Pitch Diameter

Pitch diameter estimation uses two sets of intermediate data products, the wire positions and the 3-D crest cylinder fit.

The pitch diameter estimate calculation is presented in a step-by-step list below:

a) Compute the pitch diameter contact points with the thread flanks by calculating the intersection of the wire shape with the left or right flank lines.

b) Average the left and right points of intersection, and compute the distance (radius) from the average point to the 3-D crest cylinder fit axis. This is the pitch diameter radius for each wire position.

c) Calculate the average value of the pitch diameter radius.

d) Correct each average wire position radius for the part projection angle, using the angle of the 3-D crest cylinder axis to the stage axis, projected into the sensor's coordinate system.

e) Add left and right sensor corrected pitch diameter radius estimates to produce an estimate of the pitch diameter for each view.

f) Average the laser estimates to produce the system pitch diameter estimate.

The thread cross section is specified in thread design documents. The cross section is the thread shape if it were cut by a plane going through the thread's central axis.

Calibration Correction

Pitch diameter is corrected by a final end-to-end calibration of the total system. The reported pitch diameter is often too high, with bias ranging from +5 μm to +35 μm.

After diameter calibration, one exposes the system to a set of measured thread plugs gages. One then plots their pitch diameter bias as a function of diameter and fit a simple segmented line to the bias results. These bias fits then are entered into the system calibration file and are used to correct the measured pitch diameter with the measured bias.

Lead Deviation

The lead deviation estimate uses the wire pitch and the locations of the wire positions as projected onto the 3-D cylinder fit axis.

For an ideal helical thread, the wire position projections should result in a regular pattern along the 3-D cylinder fit axis. Lead deviation is the deviation of that pattern from the ideal, measured as a maximum distance of any projected wire position from the ideal pattern.

The computation of the lead deviation estimate follows a step-by-step procedure:

a) Create a wire position projection vector, containing all the data.

b) Sort the wire position projection vector in order of position along the 3-D cylinder fit axis.

c) Convert the wire positions of the elements of the vector into degrees, by multiplying by the factor (360/pitch) and then reducing the element values modulo 360.

d) Calculate an offset value so that the maximum absolute value of the degree-valued element positions is minimal. For example with a lead deviation of 0.010 mm for a 1 mm pitch thread, the absolute value of at least one degree value element position would be 3.60 degrees (0.010) mm/1 mm equals (1/100) and 360/100 is 3.60)

Convert the value from degrees to mm and report as the lead deviation estimate.

All lead deviation estimates are positive.

Calibration Correction

Errors in measurement mean that the physical measurement of a perfect thread will have a positive lead deviation.

To attempt to correct for this effect, one measures the lead deviation for a set of thread plug gages and plotted them as a function of gage diameter. The most common form observed is a constant lead deviation of 0.010 mm to 0.20 mm.

This value observed in calibration with thread gages is taken to be a bias. This amount of bias is entered into the system calibration file and used to correct the measured lead deviation for this measurement bias.

Functional Diameter

Functional diameter is currently defined in practice by the fit of a special fit gage over the thread. The special fit gage is essentially a nut that is split in two by a plane cut through the central axis of the nut. The two halves of the fit gage are held in a fixture that measures the distance between the two halves. There is one special fit gage for every thread type.

Functional diameter is defined as the pitch diameter when the special fit gage is clamped tightly over a thread plug setting gage. When one puts a different part into the fit gage the fit gage may expand slightly, due to a summation of effects involving the differences between the part and the thread plug setting gage used to setup the functional diameter measurement. The functional diameter measurement is then the thread plug setting gage's pitch diameter plus the additional separation between the two fit gage pieces.

Functional Diameter Estimator

The functional diameter measurement method is an approximation of the fit gage method.

If we imagine the thread form as perfect and also having a 60 degree flank angle then lead deviations should cause the thread form fit gage pieces to move apart. A single lead deviation either up or down the thread form axis will cause a single split piece of the fitting gage to move outward. The amount of outward movement for a 60 degree flank angle will be equal to $(\sqrt{3})$ (lead deviation). The movement provides a clearance for both positive and negative movements of the lead, relative to a perfect helical shape.

$$FD=PD+\sqrt{3}(\text{LeadDeviation})$$

Learning the Thread Model

The thread model is a learned sequence of points that represent a best estimate of the outline of one cycle of the thread form. The thread model is calculated when the inspection region is specified, at template edit time.

The measure template routine uses a pattern match algorithm with a sine wave pattern to identify periodically in the inspection region data. This process determines an approximate thread pitch. The process also calculates a starting point in the data vector for the first beginning of the matched pattern, which is an approximation to the first midpoint of a right flank line.

With the pitch and the starting point in hand, the measure template routine can then calculate an average thread model. Starting with the first sample point in the matched pattern, points that are 1, 2, 3, ..., N pitches later in the inspection region are averaged to form the first point of the thread model. The process is repeated for all the rest of the points in the first matched pattern. The thread model is then stored in the template for later use.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A high-speed, triangulation-based, 3-D method of inspecting manufactured parts and sorting the inspected parts, each part having a length, a width, a part axis and an outer peripheral surface which extends 360° around the part, the method comprising:

receiving a supply of parts;

consecutively transferring the parts so that the parts move along a path which extends from the supply of parts and through a circumference imaging station;

supporting a plurality of angularly-spaced, triangulation-based, sensor heads at the imaging station each of the sensor heads being configured to generate focused lines of radiation and to sense corresponding reflected lines of radiation;

delivering the focused lines onto a plurality of exterior side surfaces of the part during motion of the part relative to the focused lines to obtain corresponding arrays of reflected lines of radiation, the exterior side surfaces being angularly spaced about the axis of the part at the imaging station; the sensor heads simultaneously sensing their corresponding arrays of reflected lines to obtain corresponding sets of 2-D profile signals, each set of profile signals representing a 3-D view of one of the exterior side surfaces and the sets of 2-D profile signals representing a 360° panoramic composite 3-D view of the outer peripheral surface of the part;

processing sets of 2-D profile signals of each part to identify parts having an unacceptable defect;

directing parts identified as having an unacceptable defect to a defective part area; and directing parts not identified as having an unacceptable defect to an acceptable part area.

2. The method as claimed in claim 1, wherein the step of transferring includes the step of allowing each part to fall freely so that each part is unconfined and unobstructed during the step of delivering.

3. The method as claimed in claim 1, wherein the part has a radially extending surface, wherein the focused lines are angled with respect to the radially extending surface and wherein the 3-D view includes at least a portion of the radially extending surface.

4. The method as claimed in claim 1, wherein each part is a cartridge case.

5. The method as claimed in claim 4, wherein the step of processing determines at least one of a dent, a split, a perforation, a crack, a scratch, a wrinkle, a buckle, a bulge and a surface blemish located at the side surfaces of the case.

6. The method as claimed in claim 1, wherein each of the sensor heads includes at least one semiconductor laser.

7. The method as claimed in claim 6, wherein the focused lines of radiation are polarized laser lines of light.

8. The method as claimed in claim 1, wherein each part is a threaded fastener.

9. The method as claimed in claim 8, wherein the step of processing determines a thread profile parameter.

10. The method as claimed in claim 8, wherein the step of processing identifies a thread defect.

11. A high-speed, triangulation-based, 3-D system for inspecting manufactured parts and sorting the inspected parts, each of the parts having a length, a width, a part axis and an outer peripheral surface which extends 360° around the part, the system comprising:
- a source of parts;
- a transfer subsystem for consecutively transferring the parts from the source of parts so that the parts travel along a path which extends from the source of parts and through a circumference imaging station;
- a plurality of angularly-spaced, triangulation-based, sensor heads, each of the heads being configured to generate focused lines of radiation and to sense corresponding reflected lines of radiation the heads being located at the image station to simultaneously deliver the focused lines onto a plurality of exterior side surfaces of the part during motion of the part relative to the focused lines to obtain corresponding arrays of reflected lines of radiation, the exterior side surfaces being angularly spaced about the axis of the part, the sensor heads simultaneously sensing their corresponding arrays of reflected lines to obtain corresponding sets of 2-D profile signals each set of profile signals representing a 3-D view of one of the exterior side surfaces and the sets of 2-D profile signals representing a 360° panoramic composite 3-D view of the outer peripheral surface of the part;
- at least one processor to process the sets of 2-D profile signals to identify parts having an unacceptable defect;
- a mechanism including a part sorter for directing parts identified as having an unacceptable defect to a defective part area and directing parts not identified as having an unacceptable defect to an acceptable part area; and
- a system controller coupled to the at least one processor and the part sorter to control the sorting based on the inspecting.

12. The system as claimed in claim 11, wherein the transfer subsystem includes a track adapted to consecutively receive parts to be inspected and enabling the parts to slide there along by the force of gravity.

13. The system as claimed in claim 11, wherein the part has a radially extending surface, wherein the forward lines are angled with respect to the radially extending surface and wherein the 3-D view includes at least a portion of the radially extending surface.

14. The system as claimed in claim 11, wherein each part is a cartridge case.

15. The system as claimed in claim 14, wherein at least one processor determines at least one of a dent, a split, a perforation, a crack, a scratch, a wrinkle, a buckle, a bulge and a surface blemish located at the side surfaces of the case.

16. The system as claimed in claim 11, wherein each of the sensor heads includes at least one semiconductor laser.

17. The system as claimed in claim 16, wherein the focused lines of radiation are polarized laser lines of light.

18. The system as claimed in claim 11, wherein each part is a threaded fastener.

19. The system as claimed in claim 18, wherein the at least one processor determines a thread profile parameter.

20. The system as claimed in claim 18, wherein the at least one processor identifies a thread defect.

* * * * *